(12) United States Patent
Liu et al.

(10) Patent No.: US 10,105,246 B2
(45) Date of Patent: Oct. 23, 2018

(54) HYBRID POLYMER STENT FABRICATED BY A NON-LASER CUT FABRICATION METHOD

(76) Inventors: Qing Liu, Hillsborough, NJ (US);
Zhonghua Li, Hillsborough, NJ (US)

( * ) Notice: Subject to any disclaimer, the term of this patent is extended or adjusted under 35 U.S.C. 154(b) by 1073 days.

(21) Appl. No.: 14/427,644

(22) PCT Filed: Jun. 6, 2012

(86) PCT No.: PCT/US2012/041183
§ 371 (c)(1),
(2), (4) Date: Aug. 12, 2015

(87) PCT Pub. No.: WO2012/170591
PCT Pub. Date: Dec. 13, 2012

(65) Prior Publication Data
US 2015/0335451 A1  Nov. 26, 2015

Related U.S. Application Data

(60) Provisional application No. 61/494,018, filed on Jun. 7, 2011.

(51) Int. Cl.
*B29C 64/118* (2017.01)
*B33Y 10/00* (2015.01)
(Continued)

(52) U.S. Cl.
CPC .................. *A61F 2/89* (2013.01); *A61F 2/86* (2013.01); *A61L 31/04* (2013.01);
(Continued)

(58) Field of Classification Search
CPC ...... A61F 2/89; A61F 2/86; A61F 2210/0076; A61F 2230/0069; A61F 2250/0018;
(Continued)

(56) References Cited

U.S. PATENT DOCUMENTS 4,475,972 A * 10/1984 Wong ........................ A61F 2/06
156/167
4,689,186 A * 8/1987 Bornat ...................... A61F 2/06
264/10

(Continued)

FOREIGN PATENT DOCUMENTS

WO    WO2009026200    *  2/2009

OTHER PUBLICATIONS

PCT/US2012/041183 International Search Report and Written Opinion [US] dated Dec. 11, 2012.

*Primary Examiner* — Jeffrey M Wollschlager
(74) *Attorney, Agent, or Firm* — Daniel J. Chalker; Edwin S. Flores; Chalker Flores, LLP

(57) ABSTRACT

The present invention provides a hybrid polymer stent with two or more polymer component structures which are integrated in the polymer stent main structure. The methods for fabrication of the hybrid stents is also provided. It is a further object to the present invention to provide a 4 axis RP system in which the 4th axis is a computer controlled rotation shaft added to an xyz position system. In preferred embodiments, the 4 axis RP system also has 2 or more material delivery systems that sequentially deposit two or more polymer hot melt filaments or viscous solution filaments.

21 Claims, 1 Drawing Sheet

Polymer 2       Polymer 1

Figure 1:
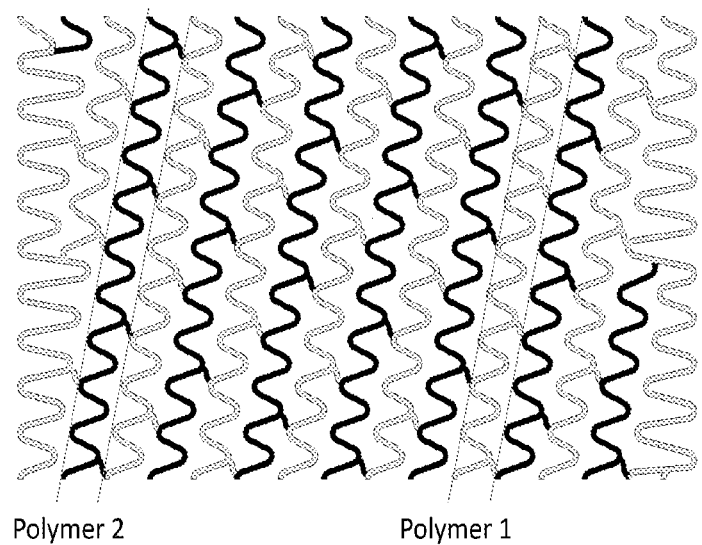

(51) Int. Cl.
*B33Y 30/00* (2015.01)
*B33Y 80/00* (2015.01)
*A61F 2/86* (2013.01)
*A61F 2/89* (2013.01)
*A61L 31/04* (2006.01)
*B29C 47/00* (2006.01)

(52) U.S. Cl.
CPC ...... *B29C 47/0014* (2013.01); *B29C 47/0016* (2013.01); *B29C 64/118* (2017.08); *A61F 2210/0076* (2013.01); *A61F 2230/0069* (2013.01); *A61F 2240/001* (2013.01); *A61F 2250/0018* (2013.01); *B33Y 10/00* (2014.12); *B33Y 30/00* (2014.12); *B33Y 80/00* (2014.12)

(58) Field of Classification Search
CPC ........... A61F 2240/001; B29C 47/0016; B29C 47/0014; B29C 67/0055; B29C 67/0092; B29C 64/118; A61L 31/04; B33Y 80/00; B33Y 10/00; B33Y 30/00
See application file for complete search history.

(56) References Cited

U.S. PATENT DOCUMENTS

| | | | | |
|---|---|---|---|---|
| 5,217,495 A * | 6/1993 | Kaplan | ...................... | A61F 2/06 57/225 |
| 5,464,450 A * | 11/1995 | Buscemi | ................... | A61F 2/82 606/154 |
| 5,629,077 A * | 5/1997 | Turnlund | .................. | A61F 2/82 156/308.2 |
| 6,056,993 A * | 5/2000 | Leidner | ..................... | A61F 2/06 427/184 |
| 6,117,535 A * | 9/2000 | Szycher | .................... | A61F 2/06 428/297.7 |
| 6,540,780 B1 * | 4/2003 | Zilla | ......................... | A61F 2/06 623/1.39 |
| 7,824,601 B1 * | 11/2010 | Stankus | .................. | A61L 31/14 264/131 |
| 7,981,353 B2 * | 7/2011 | Mitchell | .................. | A61L 27/14 264/465 |
| 8,187,319 B2 * | 5/2012 | Zilla | ......................... | A61F 2/06 623/1.39 |
| 8,741,201 B2 * | 6/2014 | Huang | ...................... | A61F 2/90 264/234 |
| 9,002,496 B2 * | 4/2015 | Elsey | .................. | B29C 67/0059 264/401 |
| 2004/0117007 A1 | 6/2004 | Whitbourne et al. | | |
| 2005/0021131 A1 * | 1/2005 | Venkatraman | ............ | A61F 2/82 623/1.19 |
| 2006/0105011 A1 * | 5/2006 | Sun | ..................... | B29C 67/0059 424/422 |
| 2006/0195179 A1 * | 8/2006 | Sun | ......................... | A61L 27/38 623/1.54 |
| 2006/0204556 A1 * | 9/2006 | Daniels | ..................... | A61F 2/82 424/443 |
| 2007/0009570 A1 * | 1/2007 | Kim | ...................... | A61L 27/18 424/423 |
| 2007/0038290 A1 * | 2/2007 | Huang | ...................... | A61F 2/90 623/1.16 |
| 2007/0270941 A1 * | 11/2007 | Headley | .................... | A61F 2/90 623/1.38 |
| 2008/0102098 A1 * | 5/2008 | Dave | ......................... | A61F 2/91 424/426 |
| 2010/0179644 A1 | 7/2010 | Jennings et al. | | |
| 2010/0256728 A1 | 10/2010 | Rea Peterson | | |
| 2010/0330144 A1 * | 12/2010 | Liu | ..................... | B05B 13/0442 424/423 |
| 2011/0196660 A1 * | 8/2011 | Liu | ..................... | B29C 47/0866 703/11 |
| 2011/0287122 A1 * | 11/2011 | Kim | ..................... | C12N 5/0062 425/174.8 R |

* cited by examiner

HYBRID POLYMER STENT FABRICATED BY A NON-LASER CUT FABRICATION METHOD

CROSS-REFERENCE TO RELATED APPLICATION

Provisional Applications 61/494,018

Sequence Listing: None

The present application claims benefit of provisional applications: 61/494,018; the disclosure of which is hereby incorporated by reference.

1. FIELD OF INVENTION

The present invention relates to a polymer stent that is used to keep a blood vessel or other body lumen open in a human body. The polymer stent has two or more polymer structure components within its main body structure. The method and apparatus for making such a polymer stent is also provided.

2. BACKGROUND OF THE INVENTION

The use of stent to keep a blood vessel or other body lumen open in a human body has become a very effective therapy to treat blood vessel stenosis and lumen obstruction. For example, using stent to treat coronary and peripheral artery blockage has become a common practice. Stents have been successfully used in keeping passageways open such as the prostate, urethral, the esophagus, the biliary tract, and intestines.

There are two types of stents that are widely used and/or studied nowadays: metallic stents and bioabsorbable polymer stents. Currently, most of the stents clinically available are metallic stents. However, there are some disadvantages that are associated with the use of metal stents. Because the metals are typically much harder and stiffer than the surrounding lumen tissue, metal stents may result in an anatomical or physiological mismatch, thereby cause irritation to the surrounding lumen tissue. The metal struts of the stents, once break after implantation, may pierce through the body lumen and causing some serious complications. The permanent irritation caused by the presence of this metallic stent will eventually cause lumen area loss due to the overgrowth of the irritated tissue. Further, metallic stents prevent lumen expansion associated with late favorable remodeling. Metal stents impair the vessel geometry and often jail and obstruct side branches.

In contrast, stents made from polymers are less stiffer than metals. Therefore, will resolve most of the above issues that are associated with the metal stents. One type of polymer stents is bioabsorbable stent. Bioabsorbable polymer stents, once they are bioabsorbed, leave behind only the healed natural vessel, allowing restoration of vasoreactivity with the potential of vessel remodeling. Late stent thrombosis is unlikely since the stent is gone, and prolonged anti-platelet therapy is not necessary in this instance.

Polymer stents can also be suitable for complex anatomy where currently used metal stents impede on vessel geometry and morphology and are prone to crush and fractures, such as in saphenous femoral and tibial arteries. Bioabsorbable stents can be used as a delivery device for agents such as drugs and genes, and may be used for treatment of vulnerable plaque.

Flexibility of the stents is one of the important characteristics. Stents have to be flexible in their crimped state in order to facilitate the delivery of the stent, for example within an artery. In some cases, stents also have to be flexible after being deployed and expanded, especially when a stent may be subjected to substantial flexing or bending, axial compressions and repeated displacements at points along its length, for example, when stenting the superficial femoral artery. This can produce severe strain and fatigue, resulting in failure of the stent.

Typically, the main body of a stent is made from a single type of material, such as stainless steel, nitinol, Co—Cr alloy, polyL-lactide. Fabrication methods, such as laser cut, braiding, and thermal forming are often been used. The mechanical properties of the stents can only be changed by the change of the structure design of the stents once the material has been chosen.

One primary goals of stent designs has been to insure that the stents have sufficient radial strength so that, when it is delivered to the intended treatment location and expanded, they can sufficiently support the lumen. Stents with high radial strength, however, tend also to have a higher longitudinal rigidity or less flexible than the vessels which are implanted. When a stent has a higher longitudinal rigidity than the vessel in which it is being treated, there is a higher chance that the rigid stent will cause trauma to the vessel at the ends of the stent, due to stress concentrations caused by the mismatch in compliance between the stented and unstented sections of the vessel. Furthermore, for a stent with higher longitudinal rigidity, after deployment in certain applications it may be subjected to substantial flexing or bending, axial compressions and repeated displacements at points along its length, for example, when stenting the superficial femoral artery. This can produce severe strain and fatigue, resulting in failure of the stent.

In a stent that is made from a single material, the mechanical properties of the stents and biological performance are largely determined by stent's structure design. It is conceivable that the mechanical and biological prosperities may be further modified if a structure component from a different type of material can be incorporated into the main structure of the stent.

Stents fabricated using a laser cut method are cut from a tube which is produced from a single material. Thus, a different structure component of a different polymer cannot be incorporated into the main stent structure during this laser cutting process. The different polymer component can only be attached to the stent main structure after obtaining the main stent structure. U.S. Patent application No. 2009 0,234,433 entitled "Helical Hybrid Stent" disclosed both a single and multi-helical structure aimed at improving the longitudinal flexibility. In this patent application, the inventors used a polymer component, such as a polymer fiber layer, attached to the outer-surface to maintain the tubular shape of the stent so that the main stent component is able to provide structural support both to the vessel and the polymer fiber layer upon deployment. In other words, polymer component is not a integrated part of the main stent structure.

We previously have filed a U.S. patent application (Liu, et al, U.S. patent application No. 2010/0330144) in which a rapid polymer stent fabrication method and system was disclosed. Unlike a laser cut stent fabrication process, this polymer stent fabrication system uses thermal plastic polymer pellets and powders to directly produce polymer stents in a single step. We further modify the system so that two or more polymers can be used and extruded in a sequential way to produce a polymer stent with two or more polymer structure component within its main body structure.

3. SUMMARY OF THE INVENTION

The present invention provides a hybrid polymer stent with two or more polymer component structures which are integrated in the polymer stent main structure. The methods for fabrication of the hybrid stents is also provided.

It is a further object to the present invention to provide a 4 axis RP system in which the 4th axis is a computer controlled rotation shaft added to an xyz position system. In preferred embodiments, the 4 axis RP system also has 2 or more material delivery systems that sequentially deposit two or more polymer hot melt filaments or viscous solution filaments. The deposited filaments adheres to the surface of the rotation shaft or bond to previously extruded filaments that are already attached to the rotation shaft. In addition, preferred embodiments allow for the fiber diameter to be changed by either varying the rotation speed of the 4th axis where the polymer filament is attached, or by varying the XY axis traveling speed, similar to a hot melt drawing process. This system is particularly suitable for making 3D tubular scaffolds, such as stents, with complicated microporous structures.

Thus, in certain embodiments, the present invention is directed to an apparatus for manufacturing a hybrid polymer stent: (i) a three-axis XYZ system connected to a base; (ii) 2 or more dispensing systems connected to the XYZ system; (iii) nozzles connected to the dispensing system; and (iv) a fourth axis system comprising a rotary rod or shaft connected to the base under the nozzle, wherein either the rotary rod, the nozzles or both are capable of moving along a longitudinal axis.

In other embodiment, the present invention is directed to a method of making a polymer stent comprising: (i) adding 2 or more polymers into each individual material delivery system in the apparatus described herein; and (ii) dispensing one polymer onto a rotary rod; and (iii) dispensing the next polymer when finishing deposition the previous polymer.

In further embodiment, the present invention is directed to a 3D tubular scaffold comprising struts and/or fibers joined in a porous three-dimensional pattern, the scaffold having an average pore size from about 1 to about 10000 microns.

In further embodiment, the present invention is directed to a special tubular scaffold called stents which are comprising struts and/or fibers joined in a pre-designed three-dimensional pattern.

4. BRIEF DESCRIPTION OF THE FIGURES

FIG. 1. A polymer stent with a double helical structure. One helical is made of polymer 1 and the other helical structure is made of polymer 2.

Figure 2:
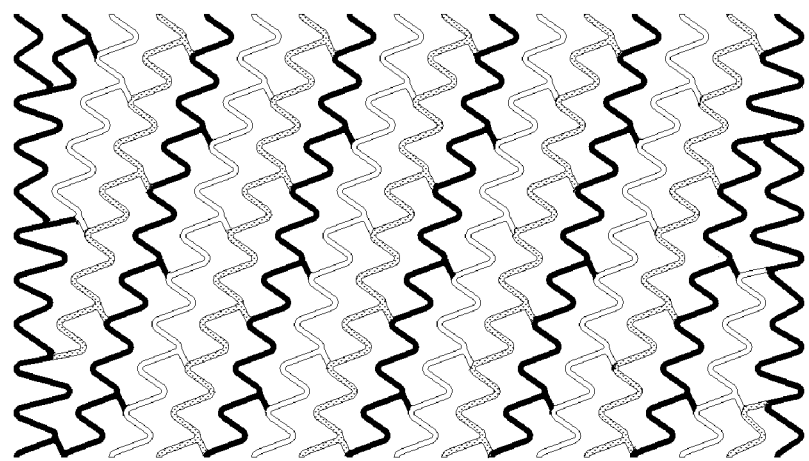

FIG. 2. A polymer stent with a triple helical structure. Each helical is made of a different polymer as shown in different color.

5. DETAILED DESCRIPTION

A polymer stent with multiple component structures and each component structure is made of a different polymers.

The polymer stent of the present invention may be made of non-biodegradable polymer, biodegradable polymer, or a combination thereof.

Non-biodegradable polymers for use in the present invention include, for example, non-degradable synthetic polymers, e.g. polyethylene terephthalate, polyamide, polyurethane, etc. and mixtures thereof.

Biodegradable polymers for use in the present invention include, but not limited to, polylactic acid (PLA), polyglycolic acid (PGA), polycaprolactone (PCL), polyanhydrides, poly($\beta$-hydroxybutyrate), polydioxanone, poly(DTH iminocarbonate), polypropylene fumarate, etc. copolymers thereof and mixtures thereof.

In the 4 axis RP system used for fabrication of the hybrid stents of the present invention, the $4^{th}$ axis is a computer controlled rotation shaft added to an xyz position system. The 4 axis RP system also has two or more material delivery systems that deposits polymer material in a hot melt filament form or a viscous solution filament form in a sequential order. The deposited filament adheres to the surface of the rotation shaft or bonds to previously extruded filaments that already attached to the rotation shaft, therefore eliminating the need to use glue or controlled heating. In addition, the fiber diameter can be controlled by either varying the rotation speed of the 4th axis where the polymer filament is attached, or by varying the XY axis traveling speed, similar to a hot melt drawing process.

The hybrid polymer stent made by the 4 axis RP system provides an additional way to control the mechanical properties of the stents. For example, in a 2 component hybrid polymer stent, one of the component structure may be made of a polymer of a high elastic module and the other component structure may be made of a rubbery polymer with low elastic modulus. The high elastic modulus polymer structure provides radius force to keep the vessel open while the low elastic component structure provide flexibility for easy delivery of stents.

The hybrid polymer stent made by the 4 axis RP system provides an additional way to control the mechanical properties of the stents during degradation. For example, in a 2 component hybrid polymer stent, one of the component structure may be made of a polymer with a fast degradation rate while the other component structure may be made of a slow degradation polymer.

The hybrid polymer stent made by the 4 axis RP system provides an additional way to control the mechanical properties change of the stents over time. For example, in a 2 component hybrid polymer stent, one of the component structure may be made of a non-degradable polymer and the other component structure may be made of biodegradable polymer. In this case, the initial radial force of the stent may start at a high level and gradually reduced to certain level when the bioabsorbable polymer component structure completely loss its mechanical strength after certain period of time post implantation.

The hybrid polymer stent of the present invention may be configured in any size to accomplish the particular purpose at hand, e.g., size suitable for use in coronary, periphery, abdomen aorta, urinary track, esophagus, bile duct, GI track, etc.

The hybrid polymer stents can be used in combination of polymer fabrics, the polymer fabric can be attached to the outside or inside of the hybrid polymer stent via any means that is known in the art, such as heating, ultra sound welding, adhesive, suture, etc.

The fibers or the struts of the hybrid polymer stents may have constant diameters or different diameters. In preferred embodiments, the diameter of the polymer fibers of the polymer stent are from about 50 micro meter to 2 mm, more preferably from 100 µm to 500 µm.

The cross sections of the struts and/or fibers may be a circle, triangle, square, rectangle, star, or irregular shape.

In certain embodiments, the hybrid polymer stents incorporate one or more biomolecules, e.g., by being coated onto the hybrid polymer stent, by being extruded together with the polymer when manufacturing the hybrid stents, or by intermixing the biomolecules with the polymers prior to manufacture. A biomolecule can be a protein, peptide, glycoaminoglycan, a naturally occurring compound or polymer, a therapeutic agent or a combination thereof. Examples of naturally occurring compound or polymer are collagen, laminin, or fibronectin. Therapeutic agents include but are not limited to, antibiotics, hormones, growth factors, anti-tumor agents, anti-fungal agents, anti-viral agents, pain medications, anti-histamines, anti-inflammatory agents, anti-infective, wound healing agents, anti-proliferative agent, wound sealants, cellular attractants, cytokines and the like. A therapeutic agent is anything that when applied to cell would benefit human health.

In certain embodiments, the hybrid polymer stents incorporate antibiotics. Antibiotics are chemotherapeutic agents that inhibit or abolish the growth of micro-organisms, such as bacteria, fungi, or protozoans. Examples of common antibiotics are penicillin and streptomycin. Other known antibiotics are amikacin, gentamicin, kanamycin, neomycin, netilmicin, tobramycin, paromomycin, geldanamycin, herbimycin, loracarbef, ertapenem, doripenem, imipenem/cilastatin, meropenem, cefadroxil, cefazolin, cefalotin or cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefdinir, cefepime, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, nafcillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, prontosil, sulfacetamide, slfamethizole, slfanilimide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin or rifampicin and tinidazole.

In certain embodiments, the hybrid polymer stents incorporate hormones. A hormone is a chemical messenger that carries a signal from one cell (or group of cells) to another via the blood. Examples of hormones are melatonin, serotonin, thyroxine, triiodothyronine, epinephrine, norepinephrine, dopamine, antimullerian hormone, adiponectin, adrenocorticotropic hormone, angiotensinogen and angiotensin, antidiuretic hormone, atrial-natriuretic peptide, calcitonin, cholecystokinin, corticotropin-releasing hormone, erythropoietin, follicle-stimulating hormone, gastrin, ghrelin, glucagon, gonadotropin-releasing hormone, growth hormone-releasing hormone, human chorionic gonadotropin, human placental lactogen, growth hormone, inhibin, insulin, insulin-like growth factor, leptin, luteinizing hormone, melanocyte stimulating hormone, oxytocin, parathyroid hormone, prolactin, secretin, somatostatin, thrombopoietin, thyroid-stimulating hormone, thyrotropin-releasing hormone, cortisol, aldosterone, testosterone, dehydroepiandrosterone, androstenedione, dihydrotestosterone, estradiol, estrone, estriol, progesterone, calcitriol, calcidiol, prostaglandins, leukotrienes, prostacyclin, thromboxane, prolactin releasing hormone, lipotropin, brain natriuretic peptide, neuropeptide Y, histamine, endothelin, pancreatic polypeptide, renin, and enkephalin, In certain embodiments, the hybrid polymer stents incorporate growth factors. Growth factor refers to a naturally occurring protein capable of stimulating cellular proliferation and cellular differentiation. Examples are transforming growth factor beta (TGF-β), granulocyte-colony stimulating factor (G-CSF), granulocyte-macrophage colony stimulating factor (GM-CSF), nerve growth factor (NGF), neurotrophins, platelet-derived growth factor (PDGF), erythropoietin (EPO), thrombopoietin (TPO), myostatin (GDF-8), growth differentiation factor-9 (GDF9), acidic fibroblast growth factor (aFGF or FGF-1), basic fibroblast growth factor (bFGF or FGF-2), epidermal growth factor (EGF), and hepatocyte growth factor (HGF).

In certain embodiments, the hybrid polymer stents incorporate antitumors. Antitumors or antineoplastics are drugs that inhibit and combat the development of tumors. Examples are actinomycin (e.g., actinomycin-D), anthracyclines (e.g., doxorubicin, daunorubicin, epirubicin), bleomycin, plicamycin, Paclitaxel and mitomycin.

In certain embodiments, the hybrid polymer stents incorporate anti-fungal agents. An anti-fungal agent is medication used to treat fungal infections. Examples are natamycin, rimocidin, filipin, nystatin, amphotericin B, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, terconazole, terbinafine, amorolfine, naftifine, butenafine, anidulafungin, caspofungin, micafungin, benzoic acid, ciclopirox, flucytosine, griseofulvin, gentian violet, haloprogin, tolnaftate, undecylenic acid, tea tree oil, citronella oil, lemon grass, orange oil, palmarosa oil, patchouli, lemon myrtle, neem seed oil, coconut oil, zinc, and selenium.

In certain embodiments, the hybrid polymer stents incorporate antiviral agents. Antiviral agents are a class of medication used specifically for treating viral infections. Examples are abacavir, aciclovir, acyclovir, adefovir, amantadine, amprenavir, arbidol, atazanavir, atripla, brivudine, cidofovir, combivir, darunavir, delavirdine, didanosine, docosanol, edoxudine, efavirenz, emtricitabine, enfuvirtide, entecavir, entry inhibitors (fusion inhibitor), famciclovir, fomivirsen, fosamprenavir, foscarnet, fosfonet, ganciclovir, gardasil, ibacitabine, imunovir, idoxuridine, imiquimod, indinavir, inosine, integrase inhibitor, interferon type III, interferon type II, interferon type I, lamivudine, lopinavir, loviride, MK-0518 (raltegravir), maraviroc, moroxydine, nelfinavir, nevirapine, nexavir, nucleoside analogues, oseltamivir, penciclovir, peramivir, pleconaril, podophyllotoxin, protease inhibitor (pharmacology), reverse transcriptase inhibitor, ribavirin, rimantadine, ritonavir, saquinavir, stavudine, synergistic enhancer (antiretroviral), tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

In certain embodiments, the hybrid polymer stents incorporate pain medications. Pain medications or analgesics (colloquially known as a painkiller) are members of the diverse group of drugs used to relieve pain. Examples are paracetamol/acetaminophen, nonsteroidal anti-inflammatory drugs (NSAIDs), COX-2 inhibitors (e.g., rofecoxib and celecoxib), morphine, codeine, oxycodone, hydrocodone, diamorphine, pethidine, tramadol, buprenorphine, tricyclic antidepressants (e.g., amitriptyline), carbamazepine, gabapentin and pregabalin.

In certain embodiments, hybrid polymer stents incorporate antihistamines. An antihistamine is a histamine antagonist that serves to reduce or eliminate effects mediated by histamine, an endogenous chemical mediator released during allergic reactions. Examples are H1 antihistamine, aceprometazine, alimemazine, astemizole, azatadine, azelastine, benadryl, brompheniramine, chlorcyclizine, chloropyramine, chlorphenamine, phenylpropanolamine, cinnarizine, clemastine, cyclizine, cyproheptadine, dexbrompheniramine, dexchlorpheniramine, diphenhydramine, doxylamine, ebastine, emedastine, epinastine, fexofenadine, histamine antagonist (e.g., cimetidine, ranitidine, and famotidine; ABT-239, thioperamide, clobenpropit, impromidine, thioperamide, cromoglicate, nedocromil), hydroxyzine, ketotifen, levocabastine, mebhydrolin, mepyramine, mthapyrilene, methdilazine, olopatadine, pheniramine, phenyltoloxamine, resporal, semprex-D, sominex, talastine, terfenadine, and triprolidine.

In certain embodiments, the hybrid polymer stents incorporate anti-inflammatory agents. Anti-inflammatory agent refers to a substance that reduces inflammation. Examples are corticosteroids, ibuprofen, diclofenac and naproxen, helenalin, salicylic acid, capsaicin, and omega-3 fatty acids.

In certain embodiments, the hybrid polymer stents incorporate anti-infective agents. Anti-infective agent is any agent capable of preventing or counteracting infection. It could be divided into several groups. Anthelminthics is one group of anti-infective agents comprising of albendazole, levamisole, mebendazole, niclosamide, praziquantel, and pyrantel. Another group is antifilarials, such as diethylcarbamazine, ivermectin, suramin sodium, antischistosomals and antitrematode medicine, oxamniquine, praziquantel, and triclabendazole. Another group is the antibacterials, which can be further subdivided. The beta lactam medicines are amoxicillin, ampicillin, benzathine benzylpenicillin, benzylpenicillin, cefazolin, cefixime, ceftazidime, ceftriaxone, cloxacillin, co-amoxiclav, imipenem/cilastatin, phenoxymethylpenicillin, and procaine benzylpenicillin. Other antibacterials are azithromycin, chloramphenicol, ciprofloxacin, clindamycin, co-trimoxazole, doxycycline, erythromycin, gentamicin, metronidazole, nitrofurantoin, spectinomycin, sulfadiazine, trimethoprim, and vancomycin. Examples of antileprosy medicines are clofazimine, dapsone, and rifampicin. Examples of antituberculosis medicines are amikacin, p-aminosalicylic acid, capreomycin, cycloserine, ethambutol, ethionamide, isoniazid, kanamycin, ofloxacin, pyrazinamide, rifampicin, and streptomycin. Examples of antifungal medicines are amphotericin B, clotrimazole, fluconazole, flucytosine, griseofulvin, nnystatin, potassium iodide. Antiviral agents are also anti-infective agents. An example of a antiherpes medicine is acyclovir. Examples of antiretrovirals are nucleoside/nucleotide reverse transcriptase inhibitors. Other examples are abacavir, didanosine, emtricitabine, lamivudine, stavudine, tenofovir disoproxil fumarate, zidovudine, non-nucleoside reverse transcriptase inhibitors, efavirenz, nevirapine, protease inhibitors, indinavir, lopinavir+ ritonavir, nelfinavir, ritonavir, saquinavir and ribavirin. Examples of antiprotozoal medicines are antiamoebic and antigiardiasis medicines such as diloxanide, metronidazole; antileishmaniasis medicines such as amphotericin B, meglumine antimoniate, pentamidine; antimalarial medicines, such as amodiaquine, artemether, artemether+lumefantrine, artesunate, chloroquine, doxycycline, mefloquine, primaquine, quinine, sulfadoxine+pyrimethamine, chloroquine, and proguanil. Antipneumocytosis and antioxoplasmosis medicines are pentamindine, pyrimethamine, sulfamethoxazole+trimethoprim. Antitrypanosomal medicines are eflornithine, melarsoprol, pentamidine, suramin sodium, benznidazole, and nifurtimox. Antimigraine medicines, acetylsalicylic acid, paracetamol, and propranolol.

In certain embodiments, the hybrid polymer stents incorporate wound healing agents. Wound healing agents facilitate the body's natural process of regenerating dermal and epidermal tissue. Examples are fibrin, fibronectin, collagen, serotonin, bradykinin, prostaglandins, prostacyclins, thromboxane, histamine, neuropeptides, kinins, collagenases, plasminogen activator, zinc-dependent metalloproteinases, lactic acid, glycosaminoglycans, proteoglycans, glycoproteins, glycosaminoglycans (GAGs), elastin, growth factors (PDGF, TGF-$\beta$), nitric oxide, and matrix metalloproteinases, Examples of wound sealants are platelet gel and fibrin.

In certain embodiments, the hybrid polymer stents incorporate anti-proliferative agents. Anti-proliferative agents prevent tissue from growth, such as to prevent restenosis (recurrent narrowing) of coronary, scar tissue formation, etc. an example of anti-proliferative agent is Paclitaxel. Applying a paclitaxel coating in a coronary stent limits restenosis or the growth of neointima (scar tissue).

In certain embodiments, the hybrid polymer stents incorporate cellular attractants. Cellular attractants or chemotaxic agents are chemicals or molecules in the environment that are sensed by bodily cells, bacteria, and other single-cell or multicellular organisms affecting their movements. Examples are amino acids, formyl peptides [e.g., N-formylmethionyl-leucyl-phenylalanine (fMLF or fMLP in references], complement 3a (C3a) and complement 5a (C5a), chemokines (e.g., IL-8); leukotrienes [e.g., leukotriene B4 (LTB4)].

In certain embodiments, the hybrid polymer stents incorporate cytokines. Cytokines are group of proteins and peptides that are signaling compounds produced by animal cells to communicate with one another. Cytokines can be divided into several families. Examples are the four alpha-helix bundle family with three subfamilies: the IL-2 subfamily [e.g., erythropoietin (EPO) and thrombopoietin (THPO)], the interferon (IFN) subfamily, the IL-10 subfamily. Other examples are the IL-1 family (e.g., IL-1 and IL-18), the IL-17 family, chemokines, immunoglobulin (Ig) superfamily, haemopoietic growth factor (type 1) family, Interferon (type 2) family, tumor necrosis factors (TNF) (type 3) family, seven transmembrane helix family, and transforming growth factor beta superfamily.

In certain embodiments, the surface or partial surface of the hybrid polymer stents can be further treated by a physiochemical mean, a chemical mean, a coating mean, or a combination thereof to improve cellular attachment.

In certain embodiments, the surface of the hybrid polymer stents can be further treated with surface modification techniques pertaining to physiochemical means known in the prior art to improve the surface property of the hybrid polymer stents for better cellular attachment, by treatment with, e.g., plasma or glow discharge.

Additionally, the surface of the hybrid polymer stents can be further surface treated by chemical means, particularly with acids or bases. In a specific embodiment, the hybrid polymer stents is treated with $H_2SO_4$, $HNO_3$, HCl, $H_3PO_4$, $H_2CrO_4$, or a combination thereof. In a specific embodiment, the hybrid polymer stents is treated with NaOH, KOH, $Ba(OH)_2$, CsOH, $Sr(OH)_2$, $Ca(OH)_2$, LiOH, RbOH, or a combination thereof.

The surface of the hybrid polymer stents may also be treated by coating means, in which a substance is applied on the surface that is different from the material of the struts and/or fibers. The substance can be covalently bonded or physically absorbed to the surface of the struts and/or fibers. Alternatively, the substance can be bonded to the surface of the construct through hydrogen bonding, ionic bonding, Van der Waals force or a combination thereof. To increase the stability of the biological molecular coating, the coating can be crosslinked using various crosslinking technologies, such as chemical crosslinking, radiation, thermal treatment, or a combination thereof, etc. Further, the crosslinking can take place in a vacuum at an elevated temperature above room temperature. The radiation used for crosslinking can be e-beam radiation, gamma radiation, ultraviolet radiation, or a combination thereof.

The coating substance can be a mixture of polymers and therapeutic agents.

The coating substance can be a protein, peptide, glycoaminoglycan, a naturally occurring substance, an inorganic substance, a therapeutic agent, or a combination thereof.

The surface of the hybrid polymer stents can be further coated with biological molecules or naturally occurring compound or polymer, such as, but not limited to, collagen (type I, II, III, IV, V, IV, etc), fibronectin, laminin, or other extracellular matrix molecules. Examples of extracellular matrix molecules are heparan sulfate, chondroitin sulfate, keratan sulfates, hyaluronic acid, elastin, hemicellulose, pectin, and extensin. The biological molecules are either covalently bonded to the surface, or physically absorbed to the surface of the tubular scaffolds.

The surface of the hybrid polymer stents can be further surface coated with a synthetic polymer, such as, polyvinyl alcohol, polyethylene glycol, polyvinyl polypyrrolidone, poly(L-lactide), polylysine, etc.

The surface of the hybrid polymer stents can also be coated with organic substance, such as gelatin, chitosan, polyacrylic acid, polyethylene glycol, polyvinyl alcohol, polyvinylpyrrilidone or a combination thereof.

Alternatively, the hybrid polymer stents may be coated with an inorganic material, such as calcium phosphate, $TiO_2$, $Al_2O_3$, or a combination thereof.

In a specific embodiment, the hybrid polymer stents are coated with a composite coating of two or more organic materials, such as, gelatin and chitosan, polyacrylic acid and polyethylene glycol, polyvinyl alcohol and polyvinylpyrilidone, etc.

The hybrid polymer stents may also be coated with a composite coating of a combination of inorganic and organic materials, such as, calcium phosphate/collagen, calcium phosphate/gelatin, calcium phosphate/polyethylene glycol, etc.

6. THE APPARATUS AND METHODS OF MANUFACTURE OF A HYBRID POLYMER STENT

In the apparatus for fabricating the hybrid polymer stent, a $4^{th}$ axis, containing a computer controlled rotation shaft, is added to an XYZ position system. This 4 axis fabrication system also has multiple materials delivery systems mounted on the XYZ position system. In preferred embodiments, the each individual materials delivery system is a polymer melt extrusion system which is able to directly deposit polymer material in a hot melt filament form, or a solution delivery system which can deliver viscous polymer solutions on to the computer controlled rotation shaft. The computer controlled rotation shaft driven by a server motor can be programmed precisely to rotation, stop and rotate back and forth at desired speeds. The rotating shaft can be equipped with a heating element or hosted in a temperature controlled environment to control the softness and viscosity of the delivered material so that the materials will exhibit the desired properties. For example, when using a polymer solution, the delivered materials can adhere better to each other and maintain a certain shape. The hot melt filament will bond to previously extruded filaments when they meet, therefore eliminating the need to use glue. For each given polymer, a set of preferred combinations of flow rate, head speed and melt chamber temperature can be established in order to produce sufficient adhesion between extrudate of adjacent polymer struts.

A hybrid polymer stent can be fabricated using above system by sequentially deposit each individual polymer onto the rotation shaft according to the stent structure design.

A hybrid polymer stent can be cut from a longer hybrid polymer stent using a mechanical device, such as a knife or a laser beam. One or more final hybrid polymer stents may be cut from a single long hybrid polymer stent.

Hot melt polymers may be used in the present invention for fabricating hybrid polymer stents. Polymer pellets/particles/beads may be used directly without pre-fabrication into polymer fibers and tubing. To realize the direct use of polymer pellets/particles/beads through hot melting, the apparatus of the present invention has 2 or more extruders which are mounted on a dispensing arm. The extruders are equipped with a delivery mechanism, such as compressed air, a plunger, a extrusion screw, or a combination of the above, to force the molten polymer through a nozzle, which is attached to the extruder. The apparatus also comprises a rotary rod positioned underneath the nozzle. The extruded polymer thin filament deposits onto the rotating rotary rod according to a designed moving pathway. The rotary rod rotates to allow the polymer to deposit on surfaces of the rod while the extruder moves along the Y-axis, thereby forming a tubular shape, with polymer melt depositing in a desired pattern. Multiple polymer components can be deposited onto the $4^{th}$ rotation axis to form a stent structure with multiple component structure. A hybrid polymer stent thus can be obtained when the solidified polymer is removed from the rotation shaft. In order to allow for greater control over porosity, pore size and structure, either the dispensing arm, rotary rod or both move along a longitudinal axis. In addition to this longitudinal movement, the speed of the rotation of the rotary rod and the speed of the longitudinal movement of the dispensing arm and/or the rotary rod can also aid in the control of strut thickness of the hybrid polymer stents.

In certain embodiments, the hybrid polymer stent of the present invention may be manufactured using a 4-axis RP system, in which multiple dispensing devices used to dispense different polymer solutions are mounted on the XYZ dispensing arm. The dispensing devices are equipped with a delivery mechanism, such as compressed air, a plunger or a combination of the two, to force the polymer solution through a nozzle or a syringe needle which is attached to the dispensing device The apparatus also comprises a rotary rod positioned underneath the nozzles. The polymer solutions are deposited in a sequential manner, i.e. first finishing deposit a polymer solution and then start the next polymer solution. Each extruded polymer solution stream deposits onto the rotating rotary according to a predetermined moving pathway or pattern. The rotary rod is equipped with a temperature control mechanism so that the polymer solutions deposited onto the rotary rod are quickly solidified or frozen, therefore, the deposited polymer solution can be kept at its deposited location and maintain certain size and shape. The freeze mechanism can be a temperature controlled freeze chamber or a rotary rod equipped with a cooling coil inside the shaft of the rod. Similar to the polymer melt deposition described above, the rotary rod rotates to allow the polymer solution to deposit on surfaces of the rod while the dispensing device moves along the Y-axis, thereby forming the 3D tubular stent structure with frozen polymer solution deposited in a particular pattern. Multiple frozen polymer solutions can be deposited on the $4^{th}$ rotation axis to form a hybrid polymer stent structure. When finishing the deposition process, the frozen polymer stent structure, along with the rotary rod, is removed from the system and put into a freeze-drying chamber. The solvent of the polymer solution is then removed through a sublime process leaving behind a solid polymer structure. When finishing the solvent removing process, a porous tubular hybrid polymer stent can be obtained when the dried polymer is removed from the rotary rod. In order to allow for greater control over strut thickness, either the dispensing arm, rotary rod or both move along a longitudinal axis. In addition to this longitudinal movement, the speed of the rotation of the rotary rod and the speed of the longitudinal movement of the dispensing arm and/or the rotary rod can also aid in the control of strut thickness of the 3D scaffold.

The present invention can use any type of thermal plastic polymer pellets, beads, particles, which are suitable for extrusion, injection molding, or forming solution with a solvent, as well as composites of two or more different thermal plastic polymer blends, inorganic particle/thermal plastic composites.

The each individual material used in each material delivery device can be a single type of thermal plastic polymer or a blend of two or more polymers in a preformed form. They can be a physical mixture of pellets/beads/particles of two or more thermoplastic polymers in a premixed mixture form. Additionally, each individual material can be a physical mixture of inorganic particles and thermoplastic polymer particles/pellets/beads. Additionally, the material can be a suspension inorganic particles suspended in a polymer solution. The materials can also be a solution from polymers and small molecules. In preferred embodiments, a micro single screw extruder is used, as it will result in a more homogeneous dispersion of inorganic particle in polymer matrix.

The material can also include a mixture of polymers and a low molecular weight substance, such as a therapeutic agent.

In certain embodiments, the polymer melt extrusion mechanism or solution dispensing device is equipped with a on/off switch or a regulator which controls the extrusion rate of the polymer melt or solution. The switch can be a pressure regulator or a pressure valve that switch the compressed air on/off when compressed gas is used for extrusion of polymer melt. When the switch is on, the polymer melt or solution will be extruded though the nozzle tip by the pressure created by the extrusion mechanism inside the melt chamber. The switch can also be a electronic switch which turns on/off the motor that controls the rotation movement of the screw in a micro single-screw extruder or in a screw driven plunger.

The diameter of the extruded/dispensed polymer filament can be controlled by the inner diameter of the extrusion/dispensing nozzle and the extrusion/dispensing speed.

7. APPLICATIONS OF THE HYBRID POLYMER STENTS

The hybrid polymer stents of the present invention may be used as vascular stents, which when placed and expanded in a plagued and narrowed segment of a blood vessel, the stent will keep the blood vessel open for easy blood flow.

The hybrid polymer stents of the present invention may be used as esophagus stents, which, when placed and expanded in a narrowed segment of a esophagus, will keep the esophagus open for easy food flow into stomach. Such an application will be advantageous for late stage esophagus cancer patients.

Similarly, the hybrid polymer stents of the present invention may also be used as stents designed for the intestines, the bile conduct, urinary tract, etc.

The hybrid polymer stents of the present invention may also be used further to make stent graft for treatment of abdominal aortic aneurysms.

The hybrid polymer stents of the present invention may also be used together with fabrics. The fabrics can be attached either to the outer surface or the inner surface or to both surfaces of the hybrid polymer stents.

The fabrics for attaching to the hybrid polymer stent can be either woven or non-woven fabrics or both.

The fabrics can be prefabricated or directly fabricated on the outer surface of the hybrid polymer stent. The direct fabrication method will included, but not limit to, an electrospinning fabrication method in which the rotation shaft with the hybrid polymer stents still on serves as the fiber collector.

What is claimed:
1. A method of making a hybrid polymer stent which has two (2) or more different polymer component structures integrated in the stent structure, the method comprising:
   (i) adding each polymer material into one of multiple dispensing systems of an apparatus for manufacturing the hybrid polymer stent, wherein the polymer materials have different elastic moduli or different degradation rates;
   (ii) forming the hybrid polymer stent having the two or more different polymer component structures by dispensing each polymer material through a nozzle onto a rotary rod according to a designed pattern, wherein the polymer component structures comprise alternating helical structures of struts or fibers of the polymer materials having a diameter of from about 50 micro meter to 2 mm that are adjacent to one another so as to be joined in a porous three-dimensional pattern; and
   wherein the apparatus comprises:
   a three-axis XYZ system connected to a base,
   the multiple dispensing systems connected to the three-axis XYZ system,
   the nozzle connected to the each dispensing system,
   a fourth axis system comprising the rotary rod connected to the base under the nozzle, wherein either the rotary rod, the nozzle or both are capable of moving along a longitudinal axis,
   wherein the multiple dispensing systems deposit the polymer material in a hot melt filament form or a viscous solution filament form in a sequential order,
   wherein the deposited filament adheres to a surface of the rotary rod or bonds to previously deposited filaments that are already attached to the rotary rod, wherein the diameter of the struts or fibers is controlled by either varying a rotation speed of the rotary rod where the polymer filament is attached, or by varying a XY axis traveling speed, and wherein the rotary rod is equipped with a heating element or hosted in a temperature controlled environment in order to produce sufficient adhesion between adjacent polymer struts or fibers.

2. The method of claim 1, further comprising drying the polymer material and removing the dried polymer material from the rotary rod.

3. The method of claim 1, wherein the stent further contains at least one therapeutic agent in at least one of the polymers in the stent.

4. The method of claim 1, wherein the struts or fibers of the hybrid polymer stent comprise an inorganic/polymer composite.

5. The method of claim 1, further comprising applying a coating on the surface of the struts or fibers of the hybrid polymer stent.

6. The method of claim 5, wherein the coating on the struts or fibers of the hybrid polymer stent is composed of a biodegradable polymer and at least one therapeutic agent.

7. The method of claim 5, wherein the coating on the struts or fibers of the hybrid polymer stent is composed of a non-biodegradable polymer and at least one therapeutic agent.

8. The method of claim 5, wherein the stent has fabrics attached either to the outer surface or the inner surface or to both surfaces of the hybrid polymer stent.

9. The method of claim 8, wherein the fabrics attaching to the hybrid polymer sent are either woven or nonwoven fabrics.

10. The method of claim 8, wherein the fabrics attaching to hybrid polymer stent are either prefabricated or directly fabricated on the outer surface of the hybrid polymer stent and wherein the direct fabrication method comprises an electro-spun fabrication method.

11. The method of claim 1, wherein the struts or fibers of the hybrid polymer stent have constant diameters.

12. The method of claim 1, wherein the polymers are all biodegradable or bioabsorbable.

13. The method of claim 1, wherein at least one of the polymers is nonbiodegradable.

14. The method of claim 1, wherein the dispensing systems of the apparatus are all polymer extruders.

15. The method of claim 1, wherein all the dispensing systems of the apparatus are syringes.

16. The method of claim 1, wherein all the dispensing systems of the apparatus are pumps.

17. The method of claim 1, wherein each of the dispensing systems of the apparatus is a combination of a polymer extruder, a syringe, and a pump.

18. The method of claim 1, wherein the apparatus further comprising a temperature control.

19. The method of claim 11, wherein the diameter of the polymer struts or fibers of the polymer stent are from 100 μm to 500 μm.

20. The method of claim 1, wherein the struts or fibers of the hybrid polymer stent have different diameters.

21. The method of claim 20, wherein the diameter of the polymer struts or fibers of the polymer stent are from 100 μm to 500 μm.

* * * * *